United States Patent [19]

Seib et al.

[11] Patent Number: 5,149,829

[45] Date of Patent: Sep. 22, 1992

[54] METHOD OF PREPARING DRY, CONCENTRATED SALTS OF ASCORBATE 2-POLYPHOSPHATE

[75] Inventors: Paul A. Seib; Xiao Y. Wang, both of Manhattan, Kans.

[73] Assignee: Hoffmann-La Roche Inc., Nutley, N.J.

[21] Appl. No.: 641,042

[22] Filed: Jan. 14, 1991

[51] Int. Cl.$^5$ .............................................. C07F 9/06
[52] U.S. Cl. .................................................. 549/222
[58] Field of Search ......................................... 549/222

[56] References Cited

FOREIGN PATENT DOCUMENTS 0231496 9/1990 Japan .
8700172 1/1987 PCT Int'l Appl. .

Primary Examiner—C. Warren Ivy
Assistant Examiner—Amelia A. Owens
Attorney, Agent, or Firm—George M. Gould; William H. Epstein

[57] ABSTRACT

A method of preparing dried, concentrated ascorbate 2-polyphosphate salts is provided wherein a starting aqueous solution containing the desired 2-polyphosphate species (as well as contaminating inorganic phosphates) as sodium and potassium salts is subjected to a sequential precipitation technique to first remove the contaminants, followed by recovery of the desired species. In preferred practice, the inital starting solution is first supplemented with calcium chloride and sufficient calcium hydroxide to adjust the pH from about 6-8, thereby causing precipitation of the inorganic contaminants. At this point the ascorbate 2-polyposphate species are recovered from the supernatant and dried. The latter preferably involves washing the precipitated organophosphate salts with an aqueous organic solvent, concentration, addition of a non-solvent such as ethanol to induce precipitation, and subsequent drying. The resulting product is a concentrated salt form of ascorbate 2-polyphosphate that is a free-flowing, dried powder which can be readily handled, stored and used as an active vitamin C supplement in food or pharmacological systems.

16 Claims, No Drawings

METHOD OF PREPARING DRY, CONCENTRATED SALTS OF ASCORBATE 2-POLYPHOSPHATE

BACKGROUND OF THE INVENTION

1. Field of the Invention

The present invention is broadly concerned with a method of preparing dry, concentrated salts of the stereoisomeric forms of ascorbate 2-polyphosphate (L-ascorbate and D-erythorbate), and particularly the calcium and magnesium salts thereof, in good yields and with a high proportion of contaminating inorganic species removed. More particularly, it is concerned with such a method wherein aqueous solutions of sodium and/or potassium L-ascorbate 2-polyphosphate are first treated by aqueous dilution, addition of $CaCl_2$ or $MgCl_2$, and pH adjustment as necessary in order to precipitate contaminating inorganic salts; the supernatant is then concentrated, and a water-miscible organic solvent is added to precipitate the desired organophosphate salts, and the final precipitate is washed to remove chloride salts and dried.

2. Description of the Prior Art

U.S. Pat. No. 4,647,672 represents a significant breakthrough in the art and describes stable, 2-polyphosphorylated species of L-ascorbic acid and its stereoisomers. The 2-polyphosphate ester of L-ascorbate described in this patent has proven to be an excellent source of vitamin C, particularly in aquatic feeds. It is furthermore believed that compounds of this type may have significant utility in human foods and pharmacological preparations.

The subject patent describes preparation of ascorbate 2-polyphosphate in liquid form, i.e., in aqueous solution. Such solutions contain significant amounts of inorganic contaminants which render them less suitable in human foods or other contexts requiring high vitamin potency or purity The '672 Patent discloses a conventional separation and purification technique for obtaining a dry product, involving use of ion exchange column chromatography. While this method does result in a dried, purified product, it is unsuitable for large-scale commercial preparation of a dried, powder-like product. The cost and technical difficulties associated with ion exchange column chromatography of polyphosphorylated L-ascorbate are formidable, and this method has not even been attempted on a commercial scale, even though the advantages of a dried, concentrated product are manifest.

There is accordingly a real and unsatisfied need in the art for an improved, low cost method for the purification and separation of salts of ascorbate 2-polyphosphate from aqueous solution which meets the twin goals of providing a dried, concentrated, powder-like product by means adapted for large-scale commercial production.

SUMMARY OF THE INVENTION

The present invention overcomes the problems described above and provides a greatly improved method for preparing dried salts of L-ascorbate 2-polyphosphate; the method gives the desired end product in good yield, with the elimination of a very high proportion of contaminating inorganic salts. At the same time, the method is eminently suited for commercial-scale operations and is low in cost.

Broadly speaking, the method of the invention involves initially providing a quantity of sodium and/or potassium ascorbate 2-polyphosphate species in aqueous solution, which also includes substantial amounts of inorganic phosphate contaminants. Such a starting solution is prepared by the methods described in U.S. Pat. No. 4,647,672, which is incorporated by reference herein.

In the next step, a member selected from the group consisting of calcium chloride and magnesium chloride is added to the starting solution, with care being taken that the concentration of inorganic contaminants present is sufficiently small to prevent formation of a gel. In this respect, if the contaminant level is too great, the entire mixture sets into a continuous gel rather than a discontinuous precipitate (inorganic salts) suspended in a continuous liquid phase (solution of organophosphates). A gel-like phase is very difficult to deal with further.

If calcium chloride is initially added, most of the inorganic phosphate salts precipitate. The pH of the mixture should next be adjusted to a level of about 6-8 by addition of calcium hydroxide, causing additional inorganic phosphate salts to precipitate, while the desired ascorbate 2-polyphosphate species from the original reaction mixture remain dissolved in the supernatant. On the other hand, if magnesium chloride is initially added, no additional base is required to obtain the desired pH level (about 7-8).

The final step of the method involves recovery of the ascorbate 2-polyphosphate species from the supernatant as a dried product. This may be accomplished by a number of techniques, but most desirably the supernatant is initially concentrated, where upon a non-solvent for the ascorbate 2-polyphosphate species which is miscible in water (e.g., ethanol) is added to the concentrated supernatant. This causes precipitation of the ascorbate 2-polyphosphate species. In order to remove sodium and/or potassium chloride from the precipitated organophosphates, the latter are contacted with a water-organic solvent mixture, and the supernatant solution is removed and discarded. Upon drying, the precipitated ascorbate 2-polyphosphate salt gives a free-flowing, powder-like product which can be conventionally stored and used in a variety of food systems for example.

DESCRIPTION OF THE PREFERRED EMBODIMENTS

In the first step of the invention, a quantity of sodium and/or potassium ascorbate 2-polyphosphate species in aqueous solution is provided, and a member selected from the group consisting of calcium chloride and magnesium chloride is added thereto. Advantageously, the molar ratio of ascorbate 2-polyphosphate to calcium or magnesium ion after such addition should be from about 1:2.5 to 1:4, and more preferably about 1:3.5. In order to inhibit the formation of an unworkable gel upon such addition, the level of inorganic phosphate contaminants in the starting aqueous solution should be no more than about 1.5% by weight as phosphorus, and more preferably not more than about 1.0% by weight as phosphorus. In order to achieve this level of contaminant concentration, it may be necessary to dilute the aqueous phosphate solution with water. As a further step to inhibit gel formation, the pH of the solution may be adjusted to a level below about 10, and most preferably below about 8.

Upon addition of the calcium or magnesium chloride, steps are taken to ensure the precipitation of at least a portion of the inorganic phosphate contaminants present in the starting solution. When calcium chloride is added, the pH is preferably adjusted as necessary to a level of about 6-8 by the addition of calcium hydroxide, but when magnesium chloride is added, no base is required. In any event, the preferred pH of the solution at this point is about 7. The mixture is then stirred for about 1-10 minutes, followed by a separation step, typically using centrifugation or filtration techniques. The supernatant is then separated from the precipitate by decantation, and the precipitated salts are serially washed and centrifuged, and the resulting supernatant solutions are combined.

The conditions employed for removing the inorganic phosphate salts also affect the proportions of the 2-triphosphate to 2-diphosphate to 2-monophosphate ester of L-ascorbate. To limit hydrolysis of the 2-polyphosphate esters to the 2-monophosphate ester during precipitation and removal of calcium or magnesium inorganic phosphates, the pH of the system should be maintained below about 10 and above about 6, and the molar ratio of $Ca^{+2}$ or $Mg^{+2}$ to L-ascorbate should be as low as possible to achieve precipitation of the inorganic phosphates. Moreover, the temperature should be maintained at a level of from about 5°-35° C., most preferably from about 10°-25° C. Furthermore, the initial reaction mixture should be diluted to a level of about 0.5% by weight phosphorus concentration, and most preferably to about 0.14% by weight phosphorus.

In order to recover the desired 2-polyphosphate species from the supernatant, the latter is first concentrated, typically by vacuum, whereupon a non-solvent for the desired ester species is added. This non-solvent must be miscible with water, and is preferably taken from the group consisting of methanol, ethanol, tetrahydrofuran, dioxane and acetone. This serves to precipitate the desired phosphate ester species, which can then be dried. Ethanol is the most preferred non-solvent, and is normally added in a volume substantially equal to that of the concentrated supernatant. Acetone is least preferred because of its volatility.

It is also desirable in most instances to remove sodium and/or potassium chloride from the precipitated ester species, prior to the final drying step. This can readily be accomplished by contacting the precipitate from the concentrated supernatant with a 1:1 v/v mixture of water and ethanol.

The following example sets forth the most preferred method in accordance with the invention. The example is provided for illustrative purposes only, and nothing therein should be taken as a limitation upon the overall scope of the invention.

EXAMPLE

A 400 ml beaker was fitted with a pH electrode, a magnetic stirring-bar, and a buret. To the beaker, which was placed in a water bath at 33°-35° C., was added in sequence, water (105 ml), L-ascorbic acid (30 g, 171 mmole, 1.63M) and 10M sodium and/or potassium hydroxide to pH about 11.0. Sodium trimetaphosphate (95-97% pure, about 232 mmole) was added, and the pH maintained at 10.5-10.7 by periodic addition of 10M sodium and/or potassium hydroxide. The reaction mixture was stirred continuously and stopped after 24 hr. reaction time. The reaction mixture, which had a total volume of about 200 ml, was diluted to volume (500 ml.) with water.

A 25 ml aliquot of the above reaction mixture (8.5 meq. of ascorbic acid in ester form) was mixed with 175 ml of water, and the mixture cooled to 10° C. Ten mls of a concentrated aqueous solution containing 25 mmole of calcium chloride was added along with 5 ml of saturated aqueous calcium hydroxide, with stirring for 6 minutes, followed by centrifugation. The supernatant was then decanted, and the precipitated inorganic salts were washed with water (3 times, 50 ml each) followed each time by centrifugation. The four supernatant solutions (about 350 ml) were then combined and vacuum evaporated below 50° C. to about 40 ml, and the concentrate was centrifuged to remove small amounts of inorganic salts. The supernatant was diluted to 90 ml, where the mixture includes about 0.1M ascorbic acid equivalents.

An equal volume of ethanol was added to the concentrated solution to precipitate the organophosphate salts. These precipitates were collected by four successive collection steps of centrifugation and washing with a 1:1 water/ethanol solution. The precipitated organic salts were then dried under reduced pressure (e.g., 50 torr) over phosphorus pentoxide.

The solid salts of L-ascorbate 2-polyphosphate contained a 3:1 molar ratio of $Ca^{+2}:Na^{+1}$ as determined by elemental assay, and the salt accounted for 87% by weight of the ascorbic acid equivalents in the original aqueous reaction mixture, as determined by UV at 258 nm and pH 10 using absorbtivity $16 \times 10^3$ mol/g cm. UV and high performance liquid chromatography showed the 3:1 $Ca^{+2}:Na^{+1}$ salt contained 78% by weight of a 1:1.86:4.50 molar mixture of L-ascorbate 2-monophosphate:L-ascorbate 2-diphosphate:L-ascorbate 2-triphosphate. The product was also found to contain 5% by weight moisture, 3% ethanol, 2% calcium orthophosphate, and less than 1% of calcium pyro-, tripoly-, or trimetaphosphate by ion-exchange chromatography. The product showed a negative chloride test when an aqueous solution thereof was treated with silver ions.

The following is a flow chart outlining the above-described procedure, which also includes a mass balance. The abbreviations used in the flow chart are also indentified below.

Mass Balance for the Isolation of CaAsPP

Reaction Mixture

-continued

Mass Balance for the Isolation of CaAsPP 0.17 moles AsA (30 g)
0.232 moles STMP (71 g)
0.50 moles NaOH (20 g)
Final water about 145 ml

↓

Make to 500 ml total volume

↓

25 ml aliquot contains

AsA, monosodium salt, 0.08 g
AsMP, trisodium salt, 0.05 g
AsDP, tetrasodium salt, 0.09 g
AsTP, pentasodium salt, 3.83 g
4-5-ene tetraP, heptasodium salt, 0.18 g
$P_i$, $PP_i$, $PPP_i$, trimetaPPP$_i$, all sodium salt, 0.949 g (1) add 175 ml H$_2$O
(2) add 10 ml of 2.5 M
   CaCl$_2$ (3.7 g), adjust
   pH 7-7.2 using 5 ml
   saturated Ca(OH)$_2$ (0.01 g)
(3) mix 6 minutes at 10° C.
(4) centrifuge

↓                              ↓

Ca inorganic phosphates        Ca/Na AsPP
wash water (50 ml)
X3

↓                              ↓

Dry                            concentrate H$_2$O (305 g removed)

↓                              ↓

Ca phosphate salts (0.955 g)   Ca/Na AsPP
CaP$_i$ 0.108 g                water (40 ml)
CAPP$_i$ 0.529 g
CaPPP$_i$ 0.318 g

↓ centrifuge

↓                    ↓ calcium phosphate    supernatant
salts (discard)      Ca/Na AsPP

↓ add water (50 ml)

↓

Ca/Na ASPP
water (90 ml)

↓ add ethanol (90 ml)

↓ centrifuge

↓                    ↓

Ca/Na AsPP (solid)   supernatant (discard)

-continued
Mass Balance for the Isolation of CaAsPP

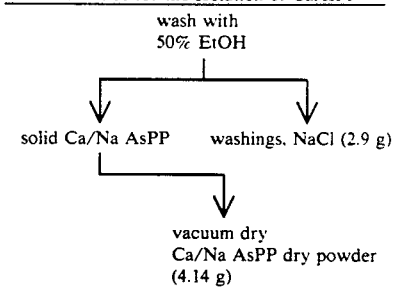

$Ca_{1.1}Na_{0.8}AsMP/Ca_{1.5}Na_{1.0}AsDP/Ca_{1.9}Na_{1.3}AsTP = 1:1.9:4.5$ (mole ratio)

Recovery of reacted AsA determined by UV = 87%
Purity of determined by UV = 78%
Expected dry mass of inorganic and organic phosphate salts = 5.18 g
Found dry mass of inorganic and organic phosphate salts = 5.10 g

| | |
|---|---|
| AsA | L-ascorbic acid |
| AsMP | L-ascorbate 2-monophosphate |
| AsDP | L-ascorbate 2-diphosphate |
| AsTP | L-ascorbate 2-triphosphate |
| STMP | Sodium trimetaphosphate |
| 4-5-ene tetraP | 4,5-Dehydrated L-ascorbate 2-triphosphate 6-phosphate |
| Pi | Orthophosphate, sodium salt |
| PPi | Pyrophosphate, sodium salt |
| PPPi | Tripolyphosphate, sodium salt |
| TrimetaPPPi | Trimetaphosphate, sodium salt |
| CaPi | Orthophosphate, calcium salt |
| CaPPi | Pyrophosphate, calcium salt |
| CaPPPi | Tripolyphosphate, calcium salt |
| Ca/Na AsPP | Calcium sodium L-ascorbate 2-polyphosphate |

We claim:

1. A method of preparing dried, concentrated ascorbate 2-polyphosphate salts, comprising the steps of:
   providing a quantity of ascorbate 2-polyphosphate species and inorganic phosphate contaminants in aqueous solution;
   adding a member selected from the group consisting of calcium chloride and magnesium chloride to said solution, with the concentration of said contaminants in said solution being sufficiently small to prevent formation of a gel, with the pH of the solution being at a level of below 10;
   precipitating at least a portion of said contaminants as the calcium or magnesium salts thereof, with the ascorbate 2-polyphosphate species from said reaction mixture remaining in the supernatant; and
   recovering said ascorbate 2-polyphosphate species from said supernatant as a dried product.

2. The method of claim 1, said contaminants being present in said solution at a level of no more than about 1.5% by weight calculated as phosphorus.

3. The method of claim 2, said contaminants being present in said solution at a level of no more than about 1.0% by weight.

4. The method of claim 3, said contaminants being present in said solution at a level of no more than about 0.14% by weight.

5. The method of claim 1, wherein calcium chloride is added to said solution, and base is added to the solution to adjust the pH thereof.

6. The method of claim 1, including the step of adjusting the temperature of said solution after addition of said member to a level of from about 5°–35° C.

7. The method of claim 6, said level being from about 10°–25° C.

8. The method of claim 1, the pH of said solution being at a level of from about 6–8.

9. The method of claim 1, the molar ratio of ascorbate 2-polyphosphate ester to calcium or magnesium ion in said solution being from about 1:2.5 to 1:4.

10. The method of claim 9, said ratio being about 1:3.5.

11. The method of claim 1, said recovering step comprising the steps of:
   concentrating said supernatant;
   adding to said concentrated supernatant a quantity of a non-solvent for said ascorbate 2-polyphosphate species which is miscible in water, and causing said species to precipitate; and
   drying said precipitated ascorbate 2-polyphosphate species.

12. The method of claim 11, including the step of washing said precipitate to remove chloride salts therefrom, prior to said drying step.

13. The method of claim 11, said non-solvent being selected from the group consisting of methanol, ethanol, tetrahydrofuran, dioxane and acetone.

14. The method of claim 13, said non-solvent being ethanol, and being added in a volume substantially equal to that of said concentrated supernatant.

15. The method of claim 12, said washing step comprising contacting said precipitate with a mixture of water and ethanol.

16. The method of claim 15, said water-ethanol mixture being about a 1:1 v/v mixture.

* * * * *